United States Patent [19]

Urline

[11] Plant 4,877

[45] Aug. 17, 1982

[54] ALMOND TREE

[75] Inventor: Fred B. Urline, 2058 Fay Dr., Atwater, Calif. 95301

[73] Assignees: Fred B. Urline; Adele Urline, both of Atwater, Calif.

[21] Appl. No.: 213,738

[22] Filed: Dec. 5, 1980

[51] Int. Cl.[3] ..... A01H 5/00

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is dense, large, vigorous, spreading in branching habit, abundantly foliated with medium size, lanceolate leaves having a finely serrate margin and alternate, globose glands, blooms heavy to very heavy with white flowers, and is a regular bearer, with heavy-to-medium productivity, of medium size, heart-shaped, non-gummy nuts having medium size, sweet-flavored kernels.

1 Drawing Figure

BACKGROUND OF THE VARIETY

1. Field of the Invention

In the course of the maintenance of an almond orchard on my ranch located near Winton, Merced County, Calif., I frequent such orchard for the purpose of inspection, cultivation, and irrigation, and—during the course of such activities—I am aware of the condition of the trees and recognize any other-than-normal growth characteristics of them. It was under such conditions that the present variety of almond tree was discovered by me.

2. Classification of the Variety

The present new and distinct variety of almond tree is embraced by Class 30, Plants, of the U.S. Patent Office Manual of Classification.

3. Prior Varieties

Among the existent varieties of almond tree which are known to me, and mentioned herein, are Nonpareil (unpatented), Mission (unpatented), and Merced (U.S. Plant Pat. No. 1,730).

ORIGIN OF THE VARIETY

The present variety of almond tree was discovered by me in an area of my ranch near the almond orchard, located as aforesaid, as one of two tree trunks—of a chance seedling—emergent from the ground. Upon close and continued observation of such one tree trunk, I confirmed my initial realization that it, and its crop, had certain novel and distinctive characteristics in comparison to the other tree trunk and known varieties such as the Nonpareil, Mission, and Merced. I, therefore, determined to effect asexual reproduction of the variety, and potentially for commercial growing.

ASEXUAL REPRODUCTION OF THE VARIETY

The present variety of almond tree was asexually reproduced by me, by budding, on my ranch located as aforesaid; such reproductions having been successful, and, in maturity, ran true in all respects to said one trunk of such chance seedling.

SUMMARY OF THE VARIETY

The herein-claimed variety of almond tree is—characteristically—dense, large, vigorous, spreading in branching habit, abundantly foliated with medium size, lanceolate leaves having a finely serrate margin and alternate, globose glands, blooms heavy to very heavy with white flowers, and is a regular bearer, with heavy-to-medium productivity, of medium size, heart-shaped, non-gummy nuts having medium size, sweet-flavored kernels.

The herein-claimed variety of almond tree is further, and particularly, characterized by blooming with the Nonpareil and Merced, and harvesting with the Merced.

BRIEF DESCRIPTION OF THE DRAWING

The drawing is an illustration, by photographic reproduction in color, of twigs with leaves and nuts in hull and—separately—nuts in hull, nuts out of hull, and kernels out of shell.

DESCRIPTION OF THE VARIETY

The botanical details of this new and distinct variety of almond tree—with color definitions (except those in common color terms) referenced to Maerz and Paul Dictionary of Color (First Edition)—are as follows:

Tree:
- *Density.*—Dense.
- *Size.*—Large.
- *Vigor.*—Vigorous.

Trunk:
- *Form.*—Stocky.
- *Texture.*—Medium.

Branches:
- *Form.*—Slender.
- *Texture.*—Smooth.
- *Lenticels.*—Few.
- *Branching habit.*—Spreading.
- *Color.*—New wood: green. Mature wood: dull brown.

Foliage:
- *Quantity.*—Abundant.

Leaves:
- *Size (Mature).*—Medium. Average length — 4". Average width — 1".
- *Shape.*—Lanceolate. Acutely pointed.
- *Thickness.*—Medium.
- *Texture.*—Smooth.
- *Margin.*—Finely serrate.
- *Petiole.*—Medium length.
- *Glands.*—Average number — 3. Alternate. Medium size. Globose. Red. Positioned on petiole.

*Color.*—Top side — medium green (23-L-8). Under side — lighter green (22-K-7).

Bloom:

*Amount of bloom.*—Heavy to very heavy.

*Color.*—White.

*Blooming period.*—Medium. Blooms with Nonpareil and Merced.

Crop:

*Bearing.*—Regular bearer.

*Productivity.*—Heavy to medium.

*Distribution of nuts on tree.*—Some in clusters on short spurs. Well distributed.

*Harvest period.*—With Merced.

*Tenacity.*—Hangs well on tree. Normal to harvest. Normal to hull.

Hull:

*Outer surface.*—Smooth.

*Pits.*—Pitted.

*Form.*—Regular.

*Thickness.*—Thick.

*Flesh.*—Fleshy.

*Suture.*—Flat depressed.

*Color.*—Light green (21-K-6) with a silvery sheen.

*Dehiscence.*—Opens partially.

*Splitting.*—Along suture.

Nut:

*Size.*—Medium. Average length — $1\frac{1}{4}''$. Average width — $1''$. Average thickness — $\frac{1}{2}''$. Average weight — 12 per ounce.

*Form.*—Length/width: ovate — heart-shaped. Width/thickness: medium.

*Shell.*—Hard — medium. Thin. Smooth. Outer shell: hard. Crumbling. Some largely missing. Some adhering to hull. Inner shell: hard. Medium seal.

*Color.*—Medium light brown (13-J-8).

*Pits.*—Few.

*Base.*—Square.

*Stem scar.*—Large.

*Apex.*—Sharp. Tip recurved.

*Wing.*—Broad. Thin. Tapered toward apex.

*Inner surface.*—Dark colored.

*Ventral streak.*—Light. Narrow. Point acute.

*Percentage of kernel to nut.*—65%.

Kernel:

*Size.*—Medium. Average length — $1''$. Average width — $\frac{5}{8}''$. Average thickness — $\frac{3}{8}''$. Average weight — 16 per ounce.

*Form.*—Length/width: ovate. Width/thickness: medium.

*Base.*—Square.

*Stem scar.*—Small.

*Apex.*—Obtuse. Acuminate. Blunt. Tip recurved.

*Texture.*—Smooth. Furrowed.

*Pellicle.*—Thin.

*Pubescence.*—Smooth. Veined.

*Color.*—Medium light brown (14-K-11).

*Number of doubles.*—Few.

*Defective kernels.*—Blanks and deformed kernels on occasion.

*Flavor.*—Sweet.

*Quality.*—Very good.

Resistance to insects and diseases: No more susceptible than any commercial variety under same growing conditions.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, particularly characterized by heart-shaped, non-gummy nuts having sweet-flavored kernels; and by blooming with the Nonpareil and Merced, and harvesting with the Merced.

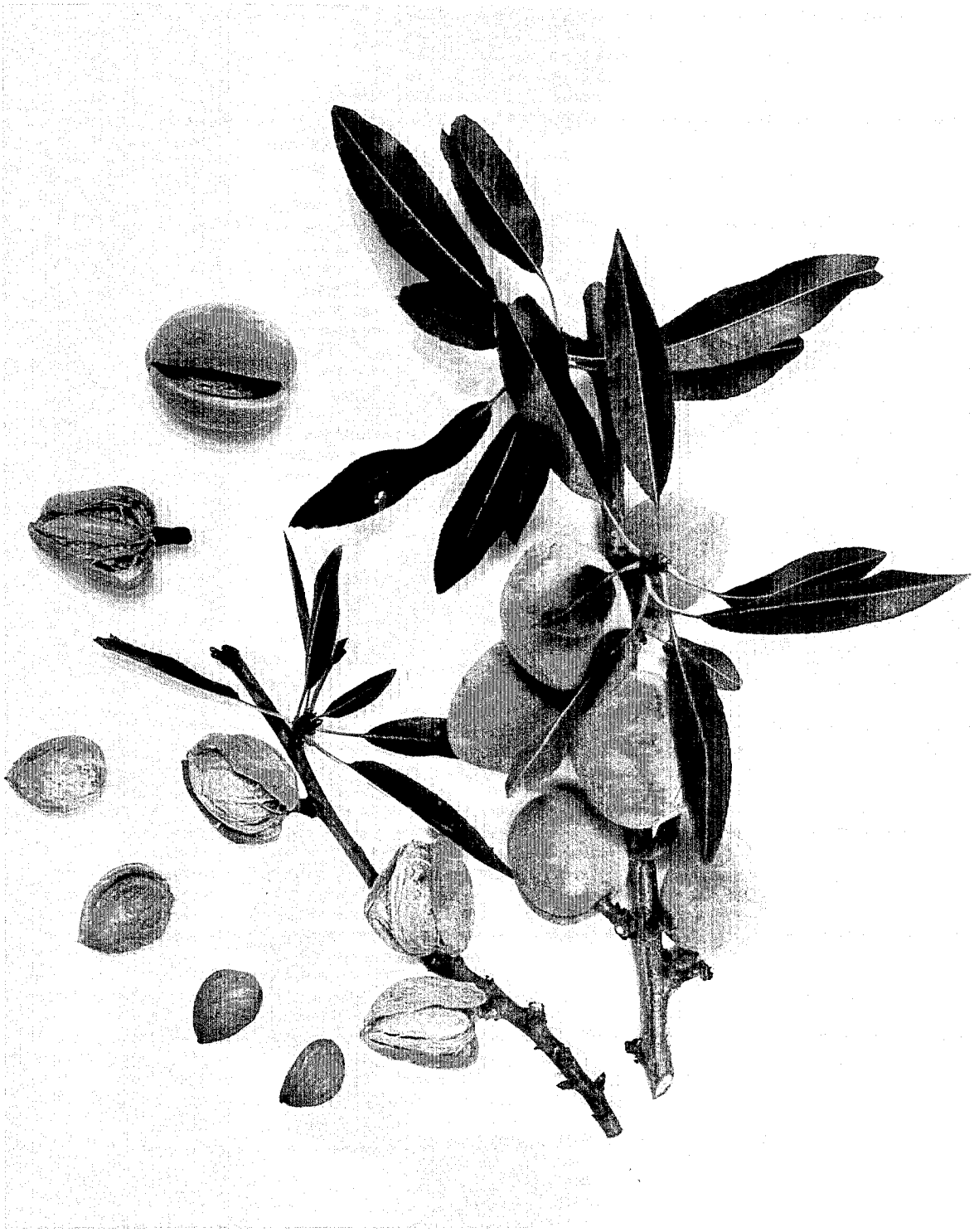

* * * * *